United States Patent
Matthews et al.

[11] Patent Number: 6,152,904
[45] Date of Patent: *Nov. 28, 2000

[54] ABSORBENT ARTICLES WITH CONTROLLABLE FILL PATTERNS

[75] Inventors: Billie Jean Matthews, Woodstock; Richard Allen Anderson, Roswell; Andrew Scott Burnes, Lawrenceville; Kuo-Shu Edward Chang, Roswell, all of Ga.; Richard Norris Dodge, II, Appleton, Wis.; Stanley Michael Gryskiewicz, Woodstock, Ga.; Connie Lynn Hetzler; Margaret Gwyn Latimer, both of Alpharetta, Ga.; Yong Li, Appleton, Wis.; Sylvia Bandy Little, Marietta; Tamara Lee Mace, Doraville, both of Ga.; James Brian Riddle, Dandridge, Tenn.; Lawrence Howell Sawyer, Roswell; Eugenio Go Varona, Marietta, both of Ga.; Hoa La Wilhelm, Appleton, Wis.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/755,136

[22] Filed: Nov. 22, 1996

[51] Int. Cl.⁷ ..................................................... A61F 13/15
[52] U.S. Cl. .......................................... 604/378; 604/367
[58] Field of Search .................................. 604/367, 378, 604/385.1, 385.2, 387

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,768,480 | 10/1973 | Mesek et al. | |
| 3,802,817 | 4/1974 | Matsuki et al. | 425/66 |
| 3,849,241 | 11/1974 | Butin et al. | 161/169 |
| 4,050,462 | 9/1977 | Woon et al. | |
| 4,100,324 | 7/1978 | Anderson et al. | 428/288 |
| 4,213,459 | 7/1980 | Sigl et al. | |
| 4,333,463 | 6/1982 | Holtman | |
| 4,340,563 | 7/1982 | Appel et al. | 264/518 |
| 4,381,783 | 5/1983 | Elias | 604/368 |
| 4,413,996 | 11/1983 | Taylor | 604/382 |
| 4,500,315 | 2/1985 | Pieniak et al. | 604/379 |
| 4,560,372 | 12/1985 | Pieniak | 604/369 |
| 4,568,341 | 2/1986 | Mitchell et al. | 604/368 |
| 4,585,448 | 4/1986 | Enloe | 604/378 |
| 4,650,479 | 3/1987 | Insley | 604/358 |
| 4,655,757 | 4/1987 | McFarland et al. | 604/366 |
| 4,673,402 | 6/1987 | Weisman et al. | 604/368 |
| 4,676,784 | 6/1987 | Erdman et al. | 604/368 |
| 4,685,915 | 8/1987 | Hasse et al. | 604/378 |
| 4,699,619 | 10/1987 | Bernardin | 604/378 |
| 4,699,620 | 10/1987 | Bernardin | |
| 4,699,823 | 10/1987 | Kellenberger et al. | 428/219 |
| 4,778,459 | 10/1988 | Fuisz | 604/378 |

(List continued on next page.)

FOREIGN PATENT DOCUMENTS

91 11161  8/1991  WIPO.

*Primary Examiner*—John G. Weiss
*Assistant Examiner*—Karin M. Reichle
*Attorney, Agent, or Firm*—James B. Robinson

[57] ABSTRACT

There is provided an absorbent system for personal care products which may be transversely divided into about an equally sized center zone, two intermediate zones and two end zones where the ratio of the amount of liquid stored in the center zone to the amount of liquid stored in at least one of the end zones 30 minutes after each of three insults of 80 ml according to a MIST Evaluation Test is less than 5:1. Such an absorbent system may be used in personal care products like diapers, training pants, feminine hygiene products, absorbent underpants, adult incontinence products, and the like.

4 Claims, 3 Drawing Sheets

U.S. PATENT DOCUMENTS

| | | |
|---|---|---|
| 4,781,710 | 11/1988 | Megison et al. ......................... 604/378 |
| 4,787,896 | 11/1988 | Houghton et al. .................... 604/385.1 |
| 4,798,603 | 1/1989 | Meyer et al. ............................ 604/378 |
| 4,818,464 | 4/1989 | Lau ......................................... 264/510 |
| 4,834,735 | 5/1989 | Alemany et al. ....................... 604/368 |
| 4,842,594 | 6/1989 | Ness ........................................ 604/368 |
| 4,885,204 | 12/1989 | Bither et al. ............................ 428/284 |
| 4,888,231 | 12/1989 | Angstadt ................................. 428/213 |
| 4,892,528 | 1/1990 | Suzuki et al. ......................... 604/385.2 |
| 4,892,532 | 1/1990 | Boman .................................... 604/366 |
| 4,892,535 | 1/1990 | Bjornberg et al. ...................... 604/380 |
| 4,923,454 | 5/1990 | Seymour et al. ....................... 604/368 |
| 4,935,022 | 6/1990 | Lash et al. .............................. 604/368 |
| 4,961,982 | 10/1990 | Taylor ....................................... 428/41 |
| 4,988,344 | 1/1991 | Reising et al. .......................... 604/368 |
| 4,988,345 | 1/1991 | Reising ................................... 604/368 |
| 5,009,650 | 4/1991 | Bernardin ............................... 604/378 |
| 5,013,309 | 5/1991 | Baigas, Jr. et al. ..................... 604/368 |
| 5,021,050 | 6/1991 | Iskra ........................................ 604/379 |
| 5,030,229 | 7/1991 | Yang .................................... 604/385.1 |
| 5,037,409 | 8/1991 | Chen et al. ............................. 604/358 |
| 5,047,023 | 9/1991 | Berg ........................................ 604/368 |
| 5,057,368 | 10/1991 | Largman et al. ....................... 428/397 |
| 5,069,970 | 12/1991 | Largman et al. ....................... 428/373 |
| 5,098,423 | 3/1992 | Pieniak et al. ....................... 604/385.1 |
| 5,108,820 | 4/1992 | Kaneko et al. ......................... 428/198 |
| 5,108,827 | 4/1992 | Gessner .................................. 428/219 |
| 5,124,188 | 6/1992 | Roe et al. ................................. 428/72 |
| 5,134,007 | 7/1992 | Reising et al. ............................ 428/78 |
| 5,843,063 | 12/1998 | Anderson et al. . |
| 5,870,973 | 10/1998 | Dodge, II et al. . |
| 5,879,343 | 3/1999 | Dodge, II et al. . |
| 5,994,615 | 11/1999 | Dodge, II et al. . |
| 6,046,377 | 4/2000 | Huntoon et al. . |

ABSORBENT ARTICLES WITH CONTROLLABLE FILL PATTERNS

BACKGROUND OF THE INVENTION

Traditional absorbent systems for personal care products store substantially all liquid insults in the crotch region. This results in the crotch region being heavily loaded with liquid by the first insult and can result in insufficient capacity for a second, third or later insult This crotch area loading can cause the product to sag away from the wearer, causing discomfort for the wearer and creating the possibility of leakage. The storage of insults in the crotch region also requires that the crotch region be wider than would be possible in a system that stored insults in a different location. A wider crotch area also causes discomfort to the wearer. Further, storage in the crotch area does not use the entire product area for storage, resulting in waste of absorbent material which is usually spread throughout the product area. Storage primarily in the crotch area would, therefore, raise product cost through the inefficient use of materials.

A system in which an insult would be accepted by a personal care product and distributed to remote areas of the product for storage away from the crotch area so that the crotch area of the product could be free to accept another insult, would be preferable to the crotch area storage design. In this context, the location of the fluid after an insult is referred to as the fill pattern. The fill pattern has a relationship to other desirable absorbent product attributes such as leakage levels from the product, ability to achieve low leakage with a narrow crotch, fit and therefore comfort to the wearer, and visual aesthetics, as noted above. A remote storage system could maximize the use of the area of the product, reduce sag and allow the production of a personal care product with a narrower, more comfortable crotch. A more efficient use of product materials should result in a lower consumer cost.

It is therefore an object of this invention to provide a personal care product having an absorbent system which may be filled in a particular order such that the insult liquid is moved to remote storage locations. Such a structure will intake a liquid insult from the wearer and move the liquid to a remote storage location in a predetermined progression and pattern of fill. It is a further object of the invention to provide personal care products with narrow crotch designs as well as personal care product designs with specific liquid storage locations.

SUMMARY OF THE INVENTION

The objects of this invention are achieved by an absorbent system having the functions of intake, controlled release, distribution, transfer and final storage and a surge layer, a distribution layer and a retention layer which are in sufficient contact to transfer liquid between them. The surge layer is capable of handling an incoming liquid insult of between about 60 and 100 cc at a volumetric flow rate of from about 5 to 20 cc/sec and has a capillary tension. The distribution layer has a capillary tension higher than the capillary tension of the surge layer and an equilibrium wicking height capillary tension of at least about 15 cm as measured by the wicking of a 8.5 g/l saline solution according to the Vertical Liquid Flux rate test throughout a life cycle of the absorbent system. The retention layer absorbs liquid quickly and efficiently from the distribution layer in a controlled manner such that liquid may be stored in a desired pattern. The retention layer also has a capillary tension higher than the capillary tension in the distribution layer throughout the life cycle of the absorbent system and is mechanically stabilized. The absorbent system is divided transversely into a center zone adjacent two intermediate zones which are each adjacent an end zone. The zones are about equally sized. A ratio of an amount of liquid stored in the center zone to an amount of liquid stored in at least one of the end zones 30 minutes after each of three insults of 80 ml according to the MIST Evaluation Test defines a fill ratio of the absorbent system which must be less than 5:1. Finally, the absorbent system has a filly saturated capacity of less than 450 g.

DEFINITIONS

Figure 1:
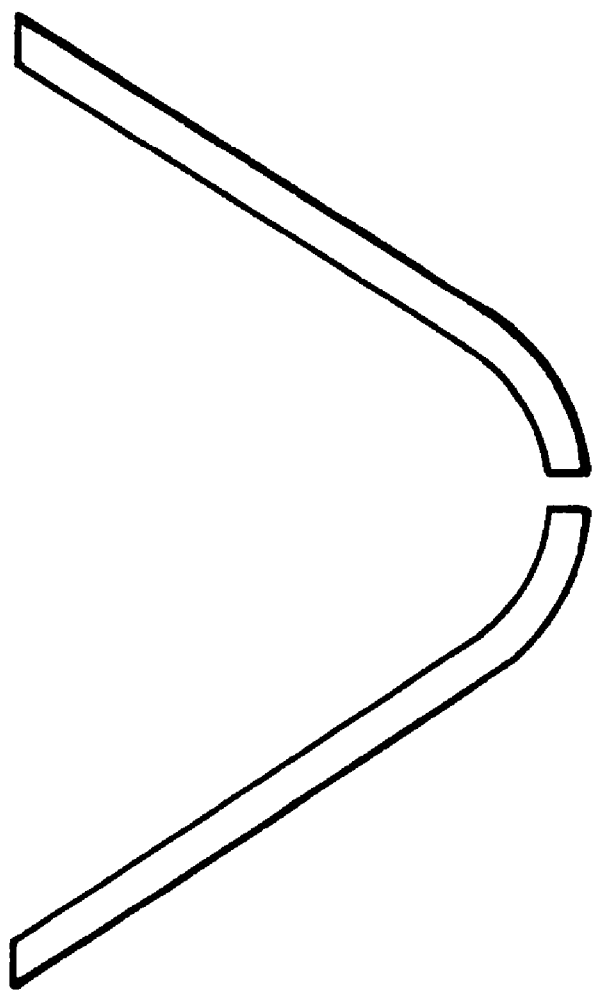
FIG. 1 is a drawing of a side view of a cradle used for the MIST Evaluation Test.

"Disposable" includes being disposed of after usually a single use and not intended to be washed and reused.

"Front" and "back" are used throughout this description to designate relationships relative to the garment itself, rather than to suggest any position the garment assumes when it is positioned on a wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Inward" and "outward" refer to positions relative to the center of an absorbent garment, and particularly transversely and/or longitudinally closer to or away from the longitudinal and transverse center of the absorbent garment.

"Layer" when used in the singular can have the dual meaning of a single element or a plurality of elements.

"Liquid" means a nongaseous substance and/or material that flows and can assume the interior shape of a container into which it is poured or placed.

"Liquid communication" means that liquid such as urine is able to travel from one location to another location.

"Longitudinal" and "transverse" have their customary meanings. The longitudinal axis lies in the plane of the article when laid flat and fully extended and is generally parallel to a vertical plane that bisects a standing wearer into left and right body halves when the article is worm. The transverse axis lies in the plane of the article generally perpendicular to the longitudinal axis.

"Particles" refers to any geometric form such as, but not limited to, spherical grains, cylindrical fibers or strands, or the like.

"Spray" and variations thereof include forcefully ejecting liquid, either as a stream such as swirl filaments, or atomized particles through an orifice, nozzle, or the like, by means of an applied pressure of air or other gas, by force of gravity, or by centrifugal force. The spray can be continuous or non-continuous.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S Pat. Nos. 5,277,976 to Hogle et al., 5,466,410 to Hills and 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent particles, natural or synthetic staple fibers, for example. Coform processes are shown in commonly assigned U.S. Pat. Nos. 4,818,464 to Lau and 4,100,324 to Anderson et al. Webs produced by the coform process are generally referred to as coform materials.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement Conjugate fibers are taught in U.S. Pat. Nos. 5,108,820 to Kaneko et al., 5,336,552 to Strack et al., and 5,382,400 to Pike et al. For two component fibers, the polymers may be present in ratios of 75/25, 50l50, 25/75 or any other desired ratios. The fibers may also have shapes such as those described in U.S. Pat. Nos. 5,277,976 to Hogle et al., and 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs that are made from staple fibers which are sent through a combing or carding unit, which separates and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding.

"Airlaying" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Personal care product" means diapers, training pants, absorbent underpants, adult incontinence products, and feminine hygiene products.

TEST METHODS

Absorption Time Index (ATI)

In this test the absorbent capacity of a superabsorbent material is determined versus time for up to 200 minutes under light pressure, e.g. about 0.01 psi.

A one inch (25.4 mm) inside diameter cylinder with an integral 100 mesh stainless steel screen on one end is used to hold 0.16±0.005 grams of dry superabsorbent. The superabsorbent should be carefully placed in the cylinder so that superabsorbent does not stick to the sides of the cylinder. The cylinder should be tapped gently to more evenly distribute the superabsorbent on the screen. A 4.4 gram, 0.995 inch (252.73 mm) diameter plastic piston is then placed in the cylinder and the cylinder, piston and superabsorbent assembly weighed. The assembly is placed in a 3 inch by 3 inch (76.4 mm by 76.4 mm) fluid basin having a 0.875 weight percent NaCl saline solution to a depth of 1 cm. Tap the cylinder gently to remove any air trapped under it and maintain the saline solution depth at 1 cm throughout the test Use a timer capable of reading 200 minutes in one second intervals. Start the timer and after 5 minutes in the solution, remove the assembly and blot on absorbent paper. A preferred paper is KLEENEX Premium Dinner Napkins from Kimberly-Clark Corp. though any other effective paper may be used. In blotting, press the paper tightly against the cylinder to ensure good contact. Touch the cylinder three times to dry paper and there should be very little liquid removed the third time. Weigh the assembly and return assembly to the fluid basin. Blotting and weighing should take about 5 seconds and the timer should be kept running throughout the test. Take readings at 5, 10, 15, 30, 45, 60, 75, 90, 120, 160 and 200 minutes. Use fresh dry napkins for each reading.

After the final reading, calculate the grams of fluid absorbed per gram of superabsorbent. The amount of liquid absorbed at particular times divided by the amount absorbed at 200 minutes may be plotted versus time for a graphical representation of the absorption rate. The ATI is calculated as follows:

$$ATI = (t_{10} + t_{20} + t_{30} + t_{40} + t_{50} + t_{60} + t_{70} + t_{80} + t_{90})/9$$

where $t_n$ is the time in minutes at which n percentage of the absorbent capacity at 200 minutes is used, e.g. $t_{30}$ is the time at which 30 percent of the total capacity is used.

Multiple Insult Test (MIST Evaluation)

In this test a fabric, material or structure composed of two or more materials is placed in an acrylic cradle to simulate body curvature of a user such as an infant. Such a cradle is illustrated in FIG. 1. The cradle has a width into the page of the drawing as shown of 33 cm and the ends are blocked off, a height of 19 cm, an inner distance between the upper arms of 30.5 cm and an angle between the upper arms of 60 degrees. The cradle has a 6.5 mm wide slot at the lowest point running the length of the cradle into the page.

The material to be tested is placed on a piece of polyethylene film the same size and shape as the sample and placed in the cradle. The material to be tested is insulted with 80 ml of a saline solution of 8.5 grams of sodium chloride per liter, at a rate of 15 cc/sec with a nozzle normal to the center of the material and ¼ inch (6.4 mm) above the material. The nozzle orifice is circular in shape with a diameter of 2.72 mm. The amount of runoff is recorded. A 0.1 psi load is placed on the material while still in the cradle using, for example, an air bladder. After 30 minutes the liquid distribution is determined, either by the x-ray imaging procedure (a non-destructive test) or the cut and weigh procedure (a destructive test). If a non-destructive test is performed, after the liquid distribution is determined the material is placed back into the cradle in the same orientation as before and the insult and liquid determination procedure repeated. This insult and liquid distribution determination is usually repeated for a total of three times. After the final insult, destructive testing may be used if desired.

X-ray imaging test

This test was one method used to determine the amount of fluid in each of the five zones of the absorbent systems. X-ray imaging is known in the art as discussed, for example, in an article entitled "Fluid Distribution: comparison of X-ray Imaging Data" by David F. Ring, Oscar Lijap and Joseph Pascente in *Nonwovens World* magazine, summer 1995, at pages 65–70. Generally, this procedure compares x-ray images of a wet and dry sample in order to calculate the liquid content. Such x-ray systems are available from Tronix Inc. of 31 Business Park Drive, Branford, Conn. 06045 as model no. 10561 HF 100 w/enclosure. This system uses software from Optumus Inc., of Ft. Collins, Colo. as BIO-SCAN OPTIMATE S/N OPM4101105461 version 4.11. The x-ray system was operated with an exposure time of 2 seconds, with a tube voltage of 50 Kv and current of 12 mA.

Capillary Tension

The capillary tension (c.t.) expressed in centimeters (cm) of the liquid is calculated from fiber and web characteristics by equating the capillary pressure exerted by the material to the hydrostatic pressure provided by a column of liquid by a method known in the art and taught in a number of references, for example *Textile Science and Technology*, vol. 7, by Pronoy K. Chatterjee, published by Elseyier Science Publishers B.V. 1985, ISBN 0-444-42377-X (vol. 7), chapters 2,4,5. These calculations assume a surface tension of 68 dynes/cm which, is taken from a 8.5 gm/l saline solution used as an approximation or simulation of urine. Urine can be quite variable in surface tension.

Capillary tension can be computed or determined experimentally by vertical wicking height testing described herein. Computations are utilized in the presence of test liquids, especially materials containing superabsorbents when exposed to saline.

| Variable | Dimensions |
|---|---|
| $c.t. = \dfrac{2}{\sqrt{\pi}} \dfrac{\gamma}{\left(\dfrac{1}{\rho_{web}} - \dfrac{1}{\rho_{avg}}\right)} \dfrac{\alpha}{980}$ | cm saline |
| $\alpha = \sum_i \dfrac{x_i}{r_{i,eff}\rho_i} \cos(\theta)$ | cm²/g |
| $\rho_{avg} = \left(\sum_i \dfrac{x_i}{\rho_i}\right)^{-1}$ | g/cm³ |
| $\rho_{web} = \dfrac{BW}{10^3 t}$ | g/cm³ |
| $r_{i,eff} = \dfrac{V_i}{SA_i}$ | cm |
| for long cylinders $r_{i,eff}(cm) = \dfrac{\frac{\pi d_i^2 L}{4}}{\pi d_i L} = \dfrac{d_i}{4 \times 10^4}$ | |
| for spheres $r_{i,eff}(cm) = \dfrac{\frac{4}{3}\frac{\pi d_i^3}{8}}{\pi d_i^2} = \dfrac{d_i}{6 \times 10^4}$ | |
| where | $\gamma$ = surface tension of fluid (dyne/cm) <br> $\theta_1$ = advancing liquid-solid contact angle (degrees) for component i <br> $\pi$ = 3.1415906 <br> $\rho_{web}$ = density of web (g/cm³) <br> $\rho_{avg}$ = mass weighted average component density (g/cm³) <br> $d_i$ = diameter of component i (microns) <br> $\rho_i$ = density of component i (g/cm³) <br> $x_i$ = mass fraction of component i in web <br> $r_{i,eff}$ = effective fiber radius (cm) <br> BW = weight of sample/area (g/m²) <br> t = thickness of sample (mm) under 0.05 psi (23.9 dyne/cm²) or 2.39 Pascal (N/m²) load |

-continued

| Variable | Dimensions |
|---|---|
| | L = cylinder length (cm)<br>$V_i$ = volume of component i (cm³)<br>$SA_i$ = surface area of component i (cm²) |

Capillary Tension Example Calculation

For a structure which contains 57% southern softwood pulp, 40% superabsorbent and 3% binder fiber, and has a basis weight of 617.58 g/m² and a bulk thickness of 5.97 mm at 0.05 psi, the example calculation of capillary tension of saline follows. The component properties are as follows:

| Component | Shape | Diameter $d_i$ (microns) | Contact Angle $\theta_1$ | Density $\rho_i$ (g/cm³) | Mass Fraction $x_i$ |
|---|---|---|---|---|---|
| So. Softwood | Cylinder | 13.3 | 45 | 1.55 | 0.57 |
| Superabsorbent | Sphere | 1125 | 30 | 1.49 | 0.40 |
| Binder fiber | Cylinder | 17.5 | 90 | 0.91 | 0.03 |

Note that the shape and contact angles are approximated.

Variable $$\alpha(cm^2/g) = \sum_i \frac{x_i}{r_{i,eff}\rho_i}\cos(\theta)$$

$$\alpha(cm^2/g) = \frac{0.57\cos(45)}{\left(\frac{13.3}{4\times 10^4}\right)\times 1.55} + \frac{0.40\cos(30)}{\left(\frac{1125}{6\times 10^4}\right)\times 1.49} + \frac{0.03\cos(90)}{\left(\frac{17.5}{4\times 10^4}\right)\times 0.925}$$

$$\alpha(cm^2/g) = 794.5$$

-continued $$\rho_{avg}(g/cm^3) = \left(\sum_i \frac{x_i}{\rho_i}\right)^{-1}$$

$$\rho_{avg}(g/cm^3) = \left(\frac{0.57}{1.55} + \frac{0.40}{1.49} + \frac{0.03}{0.925}\right)^{-1}$$

$$\rho_{avg}(g/cm^3) = 1.496$$

$$\rho_{web}(g/cm^3) = \frac{BW}{10^3 t}$$

$$\rho_{web}(g/cm^3) = \frac{617.58}{(5.97)10^3}$$

$$\rho_{web}(g/cm^3) = 0.1034$$

$$c.t.\,(cm\,saline) = \frac{2}{\sqrt{\pi}}\frac{\gamma}{\left(\frac{1}{\rho_{web}} - \frac{1}{\rho_{avg}}\right)}\frac{\alpha}{980}$$

$$c.t.\,(cm\,saline) = \frac{2}{\sqrt{\pi}}\frac{68}{\left(\frac{1}{0.1034} - \frac{1}{1.496}\right)}\frac{794.5}{980}$$

$$c.t.\,(cm\,saline) = 6.91$$

Permeability

Permeability (k) may be calculated from the Kozeny-Carman equation. This is a widely used method. References include an article by R. W. Hoyland and R. Field in the journal *Paper Technology and Industry,* December 1976, p. 291–299 and *Porous Media Fluid Transport and Pore Structure* by F. A. L. Dullien, 1979, Academic Press, Inc. ISBN 0-12-223650-5.

| | Calculated Variable | Equation | Dimensions |
|---|---|---|---|
| Permeability = | k | $= \frac{\varepsilon^3}{(KS_0^2(1-\varepsilon))^2}\frac{1}{9.87\times 10^{-9}}$ | Darcys |
| Kozeny Constant = | K | $= \frac{3.5\varepsilon^3}{(1-\varepsilon)^{0.5}}[1 + 57(1-\varepsilon)^3]$ | dimensionless |
| Surface area per mass of the material | $S_V$ | $= \sum_i \frac{x_i}{r_{i,eff}\rho_i}$ | cm²/g |
| Mass weighted average component density | $\rho_{avg}$ | $= \left(\sum_i \frac{x_i}{\rho_i}\right)^{-1}$ | g/cm³ |
| Surface area per solid volume of the material | $S_c$ | $S_V\,\rho_{avg}$ | cm$^{-1}$ |
| Porosity = | $\varepsilon$ | $= 1 - \sum_i x_i \frac{\rho_{web}}{\rho_i}$ | dimensionless |

-continued

| | Calculated Variable | Equation | Dimensions |
|---|---|---|---|
| Effective fiber radius = | $r_{i,eff}$ | $= \dfrac{V_i}{SA_i}$ | cm |
| Density of web = | $\rho_{web}$ | $= \dfrac{BW}{10^3 \cdot t}$ | g/cm$^3$ |
| for long cylinders | $r_{i,eff}$ | $= \dfrac{\frac{\pi d_i^2 L}{4}}{\pi d_i L} = \dfrac{d_i}{4 \times 10^4}$ | |
| for spheres | $r_{i,eff}$ | $= \dfrac{\frac{4}{3} \frac{\pi d_i^3}{8}}{\pi d_i^2} = \dfrac{d_i}{6 \times 10^4}$ | |
| where | $d_i =$ | diameter of component i (microns) | |
| | $\rho_i =$ | density of component i (g/cm$^3$) | |
| | $x_i =$ | mass fraction of component i in web | |
| | BW = | weight of sample/area (g/m$^2$) | |
| | t = | thickness of sample (mm) under 0.05 psi (23.9 dyne/cm$^2$) or 2.39 Pascal (N/m$^2$) load | |

Permeability Example Calculation

For a structure which contains 57% southern softwood pulp, 40% superabsorbent and 3% binder fiber, and has a basis weight of 617.58 g/m$^2$ and a bulk thickness of 5.97 mm at 0.05 psi the example permeability calculation follows.

The component properties are as follows (note shape is approximated):

| Component | Shape | Diameter $d_i$ (microns) | Density $\rho_t$ (g/cm$^3$) | Mass Fraction $x_i$ |
|---|---|---|---|---|
| Southern softwood | Cylinder | 13.3 | 1.55 | 0.57 |
| Superabsorbent | Sphere | 1125 | 1.50 | 0.40 |
| Binder | Cylinder | 17.5 | 0.925 | 0.03 |

$$\rho_{web}(g/cm^3) = \dfrac{BW}{10^3 \cdot t}$$

$$\rho_{web}(g/cm^3) = \dfrac{617.58}{(5.97)10^3}$$

$$\rho_{web}\ (g/cm^3) = 0.1034$$

$$\varepsilon = 1 - \sum_i x_i \dfrac{\rho_{web}}{\rho_i}$$

$$\varepsilon = 1 - 0.57 \dfrac{0.1034}{1.55} - 0.40 \dfrac{0.1034}{1.49} - 0.03 \dfrac{0.1034}{0.925}$$

$$\varepsilon = 0.9309$$

$$S_v(cm^2/g) = \sum_i \dfrac{x_i}{r_{i,eff}\rho_i}$$

$$S_v(cm^2/g) = \dfrac{0.57}{\left(\dfrac{13.3}{4\times 10^4}\right)\times 1.55} + \dfrac{0.40}{\left(\dfrac{1125}{6\times 10^4}\right)\times 1.49} + \dfrac{0.03}{\left(\dfrac{17.3}{4\times 10^4}\right)\times 0.925}$$

$$S_V(cm^2/g) = 1194$$

-continued

| Component | Shape | Diameter $d_i$ (microns) | Density $\rho_t$ (g/cm$^3$) | Mass Fraction $x_i$ |
|---|---|---|---|---|

$$\rho_{avg}(g/cm^3) = \left(\sum_i \dfrac{x_i}{\rho_i}\right)^{-1}$$

$$\rho_{avg}(g/cm^3) = \left(\dfrac{0.57}{1.55} + \dfrac{0.40}{1.49} + \dfrac{0.03}{0.925}\right)^{-1}$$

$\rho_{avg}\ (g/cm^3) = 1.496$
$S_0\ (cm^{-1}) = S_V\ \rho_{avg}$
$S_0\ (cm^{-1}) = 1194 \times 1.496$
$S_0\ (cm^{-1}) = 1786$ $$K = \dfrac{3.5\varepsilon^3}{(1-\varepsilon)^{0.5}}[1+57(1-\varepsilon)^3]$$

$$K = \dfrac{3.5(0.9309)^3}{(1-0.9309)^{0.5}}[1+57(1-0.9309)^3]$$

$K = 10.94$ $$k = \dfrac{\varepsilon^3}{KS_0^2(1-\varepsilon)^2}\dfrac{1}{9.87\times 10^{-9}}$$

$$k = \dfrac{(0.9309)^3}{(10.94)(1786)^2(1-0.9309)^2}\dfrac{1}{9.87\times 10^{-9}}$$

$k = 491$ darcys

Material caliper (thickness)

The caliper of materials, which is a measure of thickness, is measured at 0.05 psi with a Starret-type bulk tester, in units of millimeters.

Density

The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (g/cc). A total of three samples would be evaluated and averaged for the density values.

Wicking Time and Vertical Liquid Flux of an Absorbent Structure

A sample strip of material approximately 2 inches (5 cm) by 15 inches (38 cm) is placed vertically such that when the sample strip is positioned above a liquid reservoir at the beginning of the test, the bottom of the sample strip will just touch the liquid surface. The liquid used was a 8.5 g/l saline solution. The relative humidity should be maintained at about 90 to about 98 percent during the evaluation. The sample strip is placed above the known weight and volume of liquid and a stopwatch started as soon as the bottom edge of the sample strip touches the surface of the solution.

The vertical distance of the liquid front traveling up the sample strip and the liquid weight absorbed by the sample strip at various times is recorded. The time versus liquid front height is plotted to determine the Wicking Time at about 5 centimeters and at about 15 centimeters. The weight of the liquid absorbed by the sample strip from the beginning of the evaluation to about 5 centimeters and to about 15 centimeters height is also determined from the data. The Vertical Liquid Flux value of the sample strip at a particular height is calculated by dividing the grams of liquid absorbed by the sample strip by each of: the basis weight (gsm) of the sample strip; the time, in minutes, needed by the liquid to reach the particular height; and the width, in inches, of the sample strip. The equilibrium capillary tension is considered to be the height of liquid at the end of 30 minutes.

DETAILED DESCRIPTION

The objects of this invention are achieved by an absorbent system which includes components that have been designed, arranged, and assembled so that within a certain time after each insult, liquid will be located in a pre-specified area of the absorbent system. Such an absorbent system should not retain the bulk of the insult in the crotch area. This would allow for narrower crotch, more body-conforming articles to be produced and so result in better fit and greater comfort of the wearer, and more efficient usage of materials. When referring to diapers and training pants, a narrow crotch is one which is at most 7.6 cm in width, more particularly, at most 5 cm in width.

Fill pattern refers to the designed, preferential location of liquid in specific zones or portions of zones along the length of a product. Specific fill patterns include, but are not limited to, liquid uniformly stored throughout the product, liquid stored entirely in the front portion of the product, liquid stored entirely in the back portion of the product, and liquid stored uniformly throughout the product except for a substantially liquid free area somewhere in the product. If a liquid free area is provided, it may extend over an entire zone or may extend over part of one or several zones and be of various shapes like circles, ovals, etc. The presence of a substantially liquid free zone can be used for some other additional functional purpose such as to create a region of enhanced dryness, higher air circulation and/or a void area for storage of BM. The location of the substantially liquid free zone can be anywhere in the absorbent product. The substantially liquid free zone may be located in the crotch or target area zone, for example, to increase air circulation to help reduce the occurrence of genital inflammation. The substantially liquid free zone may be located in an intermediate zone in order, for example, to allow room for BM storage. There may be more than one liquid free zone in a personal care product. FIGS. 4 through 9 are typical example drawings of well-known personal care products.

Each fill pattern also has an associated fill progression and while fill pattern and fill progression can be the same, the invention is not limited to them being the same. For example, an absorbent system product could have a front fill pattern on the first insult, and back fill pattern on the second insult, and a bottom fill pattern on the third insult At the end of the life of such a system, the overall fill pattern is uniform, but the fill progression is front, back, bottom. As another example, for the specific embodiment that has a uniform fill pattern, the absorbent system not only has liquid uniformly distributed at the end of the life of the product (which is simulated by three insults), but has liquid substantially uniformly distributed after the first and second insults. A similar example includes embodiments which have a front fill pattern. If the embodiment has a front fill pattern after every insult, then it also has a front fill progression. This invention includes both controlled fill pattern and fill progression variations and demonstrates examples of achieving both.

Figure 2:
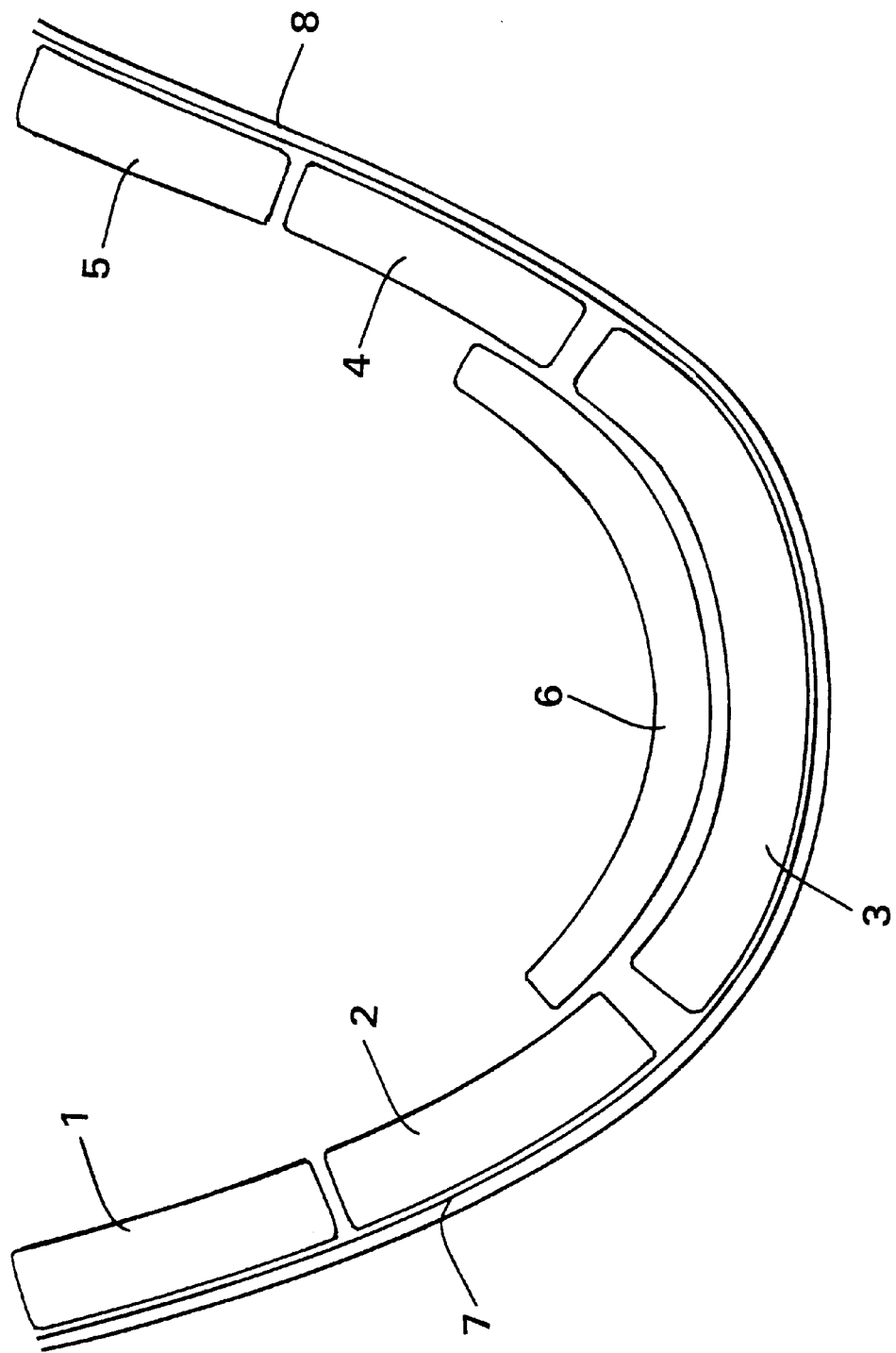
FIG. 2 is a side cutaway view of a typical personal care product such as a diaper, showing a surge layer, five retention zones, a distribution layer and a backsheet.

It is useful for the purpose of discussion and for ease of understanding to divide the absorbent system into zones along its length and discuss fill pattern in terms of fluid located in each zone at the end of some time after each insult. The absorbent systems discussed herein have been divided transversely into five zones for clarity, but it should be noted that they are not necessarily zoned in compositions or in the manufacturing process or that they are physically separated in any manner. The zones are purely for ease of understanding and illustration of the location of liquid in the absorbent system of a personal care product. Along the length of the product, the transverse zones are arbitrarily defined and divided to be approximately equal to one fifth of the overall product length, or, in the Examples, about three inches (7.6 cm) each. FIG. 2 shows a side view of a typical absorbent system where the retention material alone is divided into five zones 1–5 numbered from the front of the article to the back; the center target zone 3, two end retention zones (front and back) 1,5 respectively and two intermediate zones (front and back) 2, 4 respectively. The center target zone 3, if the absorbent system were part of a personal care or feminine hygiene product, would be generally located at the position where an insult would be delivered by a wearer. The absorbent article of FIG. 2 also includes a surge material 6, a distribution material 7, and a backsheet 8.

In the Examples, the width of each zone is about three inches in the rectangular absorbent system examples. The width of the zone is variable in shaped absorbent systems. This invention applies to both rectangular and shaped absorbent system products, and while the specified number of zones, 5, is for illustrative purposes only, more or less zones could be included for different illustrations of the invention.

A ratio of grams of fluid located in the center target zone 3 to each of the end retention zones 1, 5 is defined as the fill ratio. The fill ratio is calculated by dividing the grams of fluid in the center zone 3 by the grams of fluid in each of the end retention zones 1, 5 after the specified time; In order to fall within the scope of this invention, this center:end fill ratio is less than 5:1 after a first insult, a second insult and after each of three insults, for at least one end zone. Its preferred that the center:end fill ratio be less than 3:1, and most preferred to be less than 2.5:1. It should be noted that although the testing to determine center: end fill ratios herein uses a vertically oriented absorbent system, the invention is independent of the position in which the system is tested, i.e. a prone or side oriented absorbent system should provide the same results.

The grams of fluid in a zone may be determined simply by cutting the absorbent system into approximately equally sized pieces corresponding to the zones, weighing each zone and comparing each zone wet weight to a known dry weight. The partitioning of fluid in each zone may also be determined by the x-ray procedure given in the Test Methods section.

Absorbent systems which meet the fill ratio requirement move a substantial portion of the liquid out of the target zone and benefit the product by preparing it for multiple insults. Another result of such low fill ratio absorbent systems is lower first and subsequent insult run-off values than absorbent systems that preferentially hold liquid in the target zone. Systems that preferentially hold liquid in the target zone are referred to herein as high fill ratio systems and also have higher second and third insult run-off values than low fill ratio absorbent systems. Potential leakage levels are predicted by liquid run-off values from controlled bench tests. The absorbent systems within the scope of this invention should have less than 40 ml of total run-off from three 80 ml insults (240 ml total insult volume) delivered at a rate of 15 ml/second at 30 minute intervals. This functional performance characteristic must be achieved with an absorbent system product having a fully saturated capacity of less than 450 g.

Traditional absorbent systems for personal care products may be generalized as having the functions of surge control and containment (retention) or SC.

Surge control materials, the "S" in SC, are provided to quickly accept the incoming insult and either absorb, hold, channel or otherwise manage the liquid so that it does not leak outside the article. The surge layer may also be referred to as an intake layer, transfer layer, transport layer and the like. A surge material must typically be capable of handling an incoming insult of between about 60 and 100 cc at a volumetric flow rate of from about 5 to 20 cc/sec, for infants, for example. Surge control is typically provided by a fluff pulp in an absorbent product or by a high permeability nonwoven layer.

Containment or retention materials, the "C" in SC, must absorb the insult quickly and efficiently. They should be capable of absorbing the liquid without significant "gel blocking" or blocking of penetration of liquid further into the absorbent by the expansion of the outer layers of absorbent. Retention materials are often composites containing high rate superabsorbent polymers such as blends of polyacrylate superabsorbent and fluff. These materials rapidly absorb and hold liquid.

In addition to the surge control and containment materials in traditional absorbent systems, recent work has introduced another layer interposed between the S and C layers. This new layer is a distribution layer, producing a system with surge control, distribution and containment or "SDC". While it may appear obvious, it should be noted that in order to function effectively, the materials used in this invention must have sufficient contact to transfer liquid between them.

Distribution materials, the "D" in SDC, must be capable of moving fluid from the point of initial deposition to where storage is desired. Distribution must take place at an acceptable rate such that the target insult area, generally the crotch area, is ready for the next insult. By "ready for the next insult" it is meant that sufficient liquid has been moved out of the target zone so that the next insult results in liquid absorption and runoff within acceptable volumes. The time between insults can range from just a few minutes to hours, generally depending on the age of the wearer. It should be noted that the simple addition of a distribution material to current absorbent systems is not sufficient to achieve the benefits of the instant invention. Such a system may cause some liquid to move to remote areas but this movement is limited in volume especially when working against a negative hydrostatic head caused, for example, by a height differential between the target zone and remote areas. Such a system will result in preferential filling of target zone capacity before substantial movement of liquid to remote storage areas.

Absorbent products such as, for example, diapers, generally also have a liner which goes against the wearer, a backsheet which is the most exterior layer, and may also contain other layers such as the multifunctional materials described in patent application Ser. No. 08/754,414, filed the same day and assigned to the same assignee as this application and entitled MULTIFUNCTIONAL ABSORBENT MATERIALS AND PRODUCTS MADE THEREFROM.

The liner is sometimes referred to as a bodyside liner or topsheet and is adjacent the surge material. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner, including spunbond or meltblown webs of polyolefin, polyester, polyamide (or other like fiber forming polymer) filaments, or bonded carded webs of natural polymers (for example, rayon or cotton fibers) and/or synthetic polymers (for example, polypropylene or polyester) fibers. For example, the bodyside liner can be a nonwoven spunbond web of synthetic polypropylene filaments. The nonwoven web can have a basis weight (for example, ranging from about 10.0 grams per square meter (gsm) to about 68.0 gsm, and more particularly from about 14.0 gsm to about 42.0 gsm, a bulk or thickness ranging from about 0.13 millimeter (mm) to about 1.0 mm, and more particularly from about 0.18 mm to about 0.55 mm, and a density between about 0.025 grams per cubic centimeter (g/cc) and about 0.12 g/cc, and more particularly between about 0.068 g/cc and about 0.083 g/cc. Additionally, the permeability of such nonwoven web can be from about 150 Darcy to about 5000 Darcy. The nonwoven web can be surface treated with a selected amount of surfactant, such as about 0.28% TRITON X-102 surfactant, or otherwise processed to impart the desired level of wettability and hydrophilicity. If a surfactant is used, it can be an internal additive or applied to the web by any conventional means, such as spraying, printing, dipping, brush coating and the like.

The surge layer is most typically interposed between and in intimate, liquid communicating contact with the bodyside liner and another layer such as a distribution or retention layer, or the multifunctional material of copending application entitled MULTIFUNCTIONAL ABSORBENT MATERIALS AND PRODUCTS MADE THEREFROM.

The surge layer is generally subjacent the inner (unexposed) surface of bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solventbased and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer. One exemplary surge material may be found in U.S. patent application Ser. No. 08/755,514, filed the same day and assigned to the same assignee as this application and entitled HIGHLY EFFICIENT SURGE MATERIAL FOR ABSORBENT ARTICLES which presents a surge material which is a wettable web of fibers of at most 30 microns in diameter where the web has a permeability between about 250 and 1500 Darcys, a capillary tension between about 1.5 and 5 cm, and which maintains that permeability and capillary tension over the life of the web. Its preferred that the web have a density between about 0.02 g/cc to about 0.07 g/cc. Various woven fabrics and nonwoven webs can be used to construct a surge layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded carded web or an airlaid web composed of natural and/or synthetic fibers. The bonded carded web may, for example, be a powder bonded carded web, an infrared bonded carded web, or a through-air bonded carded web. The carded webs can optionally include a mixture or blend of different fibers, and the fiber lengths within a selected web may range from about 3 mm to about 60 mm.

The distribution layer must be capable of moving fluid from the point of initial deposition to where storage is desired. Distribution must take place at an acceptable rate such that the target insult area, generally the crotch area, is ready for the next insult. The time between insults can range from just a few minutes to hours, generally depending on the age of the wearer. In order to achieve this transportation function, a distribution layer must have a high capillary tension value. Capillary tension in distribution materials is measured simply by the equilibrium wicking of a 8.5 g/l saline solution according to the Vertical Liquid Flux rate test, not by the test method given for materials containing superabsorbents. A successful distribution layer must have a capillary tension greater than the adjacent layer (on the side toward the wearer) and preferably an equilibrium wicking height capillary tension of at least about 15 cm. Because of the generally inverse relationship between capillary tension and permeability, such a high capillary tension indicates that the distribution layer will usually have a low permeability.

Another liquid transport property desired of a suitable distribution material is that it exhibit a Vertical Liquid Flux rate, at a height of about 15 centimeters, suitably of at least about 0.002 grams of liquid per minute per square meter (gsm) of distribution material per inch of cross-sectional width of the distribution material g/(min*gsm*inch), up to about 0.1 g/(min*gsm*inch). As used herein, the Vertical Liquid Flux rate value of a distribution material is meant to represent the amount of liquid transported across a boundary a specified vertical distance away from a centralized liquid insult location per minute per normalized quantity of the distribution material. The Vertical Liquid Flux rate, at a height of about 15 centimeters, of a distribution material may be measured according to the test method described herein.

Another liquid transport property desired of a distribution material is that it exhibit a Vertical Liquid Flux rate, at a height of about 5 centimeters, suitably of at least about 0.01 g/(min*gsm*inch) up to about 0.5 g/(min*gsm*inch). The Vertical Liquid Flux rate, at a height of about 5 centimeters, of an absorbent structure may be measured according to the test method described herein.

Materials from which the distribution layer may be made include woven fabrics and nonwoven webs, foams and filamentious materials. For example, the distribution layer may be a nonwoven fabric layer composed of a meltblown or spunbond web of polyolefin, polyester, polyamide (or other web forming polymer) filaments. Such nonwoven fabric layers may include conjugate, biconstituent and homopolymer fibers of staple or other lengths and mixtures of such fibers with other types of fibers. The distribution layer also can be a bonded carded web, an airlaid web or a wetlaid pulp structure composed of natural and/or synthetic fibers, or a combination thereof.

As described in the previously cited, co-owned patent application MULTIFUNCTIONAL ABSORBENT MATERIALS AND PRODUCTS MADE THEREFROM, the multifunctional material has been designed to assist the surge material 1) by accepting a portion of the insult volume during forced flow, i.e. during an actual insult, 2) by desorbing the surge material of liquid during and after insults, 3) by allowing a portion of the insult volume to pass through itself (the multifunctional material) to the distribution material and 4) by permanently absorbing a portion of the liquid insult. The basic structure of the multifunctional material is a unique blend of superabsorbent material, high bulk wet resilient pulp, and a structure stabilizing component such as a binder which may be a fiber, liquid or other binder means. Exemplary binders include conjugate fibers of polyolefins and/or polyamides, homopolymer microfibers like meltblown polypropylene fibers in a coform with the other ingredients to entangle and/or bond them, and liquid adhesives. The multifunctional material has a permeability of between about 100 and 10000 Darcys, a capillary tension between about 2 and 15 cm, and a runoff rate of less than 25 ml per 100 ml insult, over its life. The "life" of the multifunctional material is considered to be three insults of 100 ml each where each insult is separated by 30 minutes. In order to achieve the required capillary tension and permeability, its preferred that the multifunctional material have between 30 and 75 weight percent of slow rate superabsorbent, between 25 and 70 weight percent of pulp and from a positive amount up to about 10 percent of a binder component. The material should have a density between about 0.05 and 0.5 g/cc. The basis weight of the material will vary depending on the product application but should generally be between about 200 and 700 gsm. By "slow rate" superabsorbent what is meant is a superabsorbent having an absorption time index (ATI) of at least 5 minutes and preferably more than 10 minutes.

The backsheet is sometimes referred to as the outer cover and is the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Backings may also serve the function of a mating member for mechanical fasteners, in the case, for example, where a nonwoven fabric is the outer surface.

The retention materials used in this invention must absorb liquid from the distribution layer in a controlled manner such that liquid may be stored in the desired pattern. Suitable retention materials for this application should contain an absorbent composition comprising from 20 to 85 weight percent of superabsorbent, from 80 to 0 weight percent pulp, from a positive amount to about 10 weight percent of a binder component and which has a density between about 0.1 and 0.4 g/cc. The retention materials must, of course, be mechanically stable in order to survive dry and wet use conditions. The integrity of the retention materials may be provided by small amounts of thermally activated conjugate binder fiber, for example, or by any other suitable means such as with liquid adhesives, heat activated film adhesives, or with meltblown fibers which bind the other ingredients mechanically (by entanglement) or adhesively. An example of suitable retention materials may be found in U.S Pat. No. 5,350,370 to Jackson et al. commonly assigned.

In the Examples that follow the surge material that was used was 90% by weight 3 denier conjugate PE/PET sheath/core fibers with the durable wettable nature in this web being supplied by a cellulosic (1.5 denier rayon) present at 10% by weight. A web very similar to this web is described in the copending patent application entitled HIGHLY EFFICIENT SURGE MATERIAL FOR ABSORBENT ARTICLES where it is Example 1.

EXAMPLE 1

Example 1 is a layered absorbent system with specific components designed to provide needed functions as well as a specific arrangement of components to provide designed interactions of functions. Example 1 illustrates an embodiment in which fluid is distributed to and deposited in all five zones at the end of each of the insult cycles, e.g. after 30 minutes from the insult. This Example 1 shows uniform fill progression for a uniform fill pattern.

The functions that the materials and system must exhibit are intake (surge), controlled release, distribution, transfer, and final storage. The movement of liquid into and throughout the system is controlled by a capillarity balance from one material relative to another throughout the life cycle of the system.

The surge material is a non-woven fabric with a capillary tension capability of 1.5 cm–5 cm, with a permeability range capability of 250–1500 Darcys. The surge material used in these Examples is 3 inch (7.6 cm) by 5 inch (12.6 cm) bonded carded web consisting of 90% 3 denier conjugate polyethylene/polyethylene terephthalate, (PE/PET) BASF 1053 fiber blended with 10 weight percent 1.5 denier Courtaulds rayon fiber at 400 gsm and 0.028 g/cc density. The BASF fibers are available from BASF Fibers, 6805 Morrison Boulevard, Charlotte, N.C. 28211–3577 and were conjugate sheath/core polyethylene/polyethylene terephthalate (PEIPET) fibers with a polyethylene glycol based C S-2 finish. The rayon fibers were 1.5 denier Merge 18453 fibers from Courtaulds Fibers Incorporated of Axis, Ala.

Figure 3:
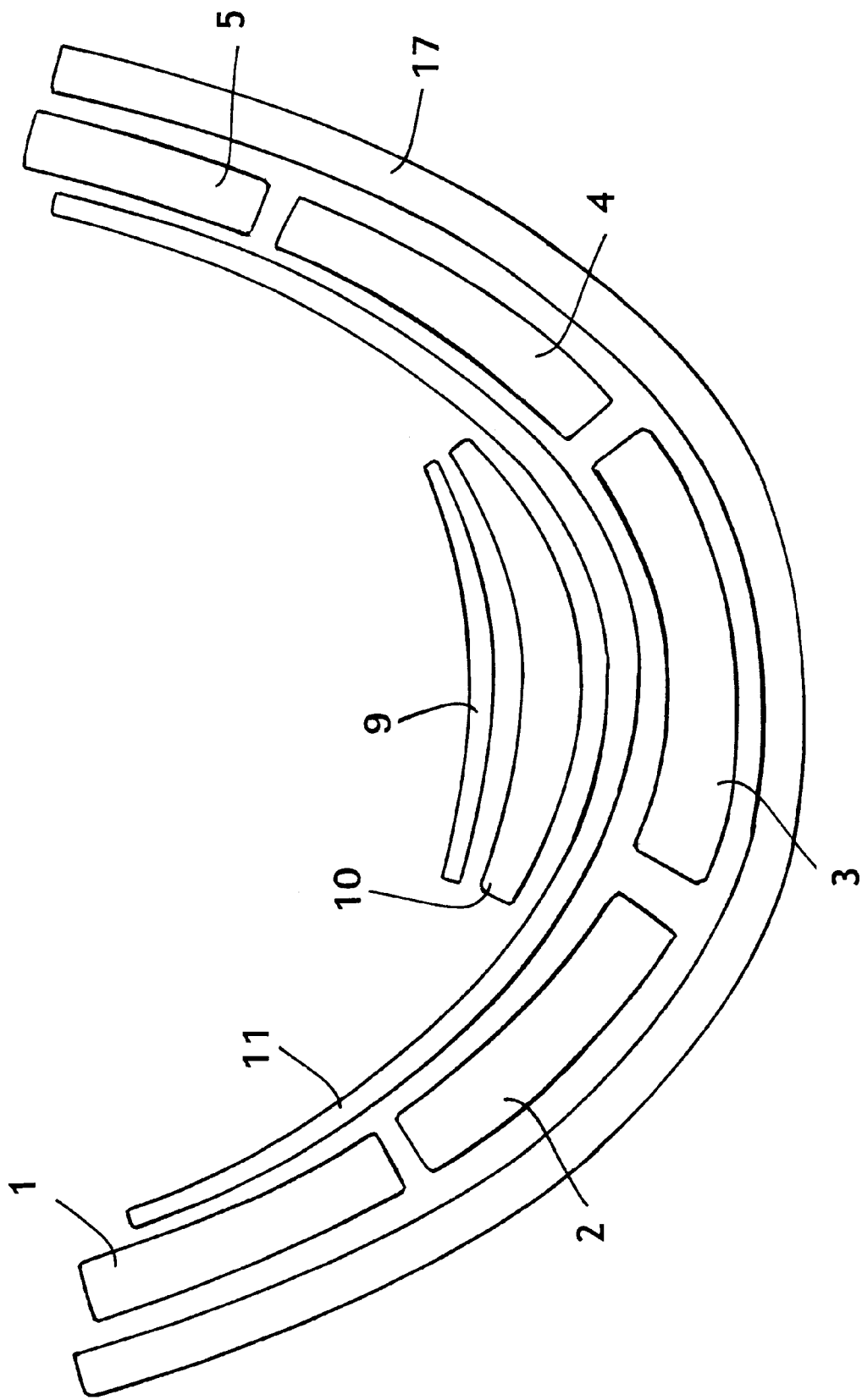
FIG. 3 is a side cutaway view of a personal care product such as a diaper as described in Example 1 showing a surge layer, a multifunctional material, five retention zones, a distribution layer and a backsheet.

As illustrated in FIG. 3, the surge material 9 is in liquid communication with a multifunctional material 10 that is also in the crotch region and provides some additional intake capability. It also provides temporary liquid storage, as well as release to the underlying distribution material 11, and permanent storage of some fluid. The multifunctional material 10 has to have and maintain a capillary tension level above the capillary tension level of the surge material 9 in order to desorb it. Similarly it has to have a capillary tension level below that of the distribution material 11 in order to release to it In this Example, the required capillarity level is achieved and maintained with a multifunctional material consisting of a blend of 40 weight percent slow superabsorbent which was AFA-94-21-5 from The Dow Chemical Company of Midland Mich., 57 weight percent Weyerhaeuser HBAFF pulp, and 3 weight percent Danakion PE/PP binder fiber. Additionally, the permeability range for the multifunctional material s is 100 to 10000 Darcys. Moreover, the slow superabsorbent component within the multifunctional material 10 stores only a portion of the liquid in the crotch region. The remaining liquid can be released to the distribution material 11 for movement to and storage in remote locations away from the crotch area.

The distribution material 11 is the component that carries liquid away from the multifunctional material 10 and delivers it to and transfers it to remote storage areas. As shown in FIG. 3 these storage areas are the center zone 3, the front intermediate zone 2, the front end zone 1, the back intermediate zone 4 and the back end zone 5. Also provided in FIG. 3 is a backsheet 17. The distribution material 11 has to have a capillary tension level above that of the multifunctional material 10 in order to desorb it. The distribution material 11 also has to have enough capillary tension capability to carry liquid up to 15 cm–25 cm in vertical height in order to feed both the intermediate retention zones 2, 4 and the end retention zones 1, 5. When the user of the product is in a standing position, vertical heights between 15 and 25 cm for the end zone are common.

The distribution material in these Examples consists of two 100 gsm layers of chemically stiffened Northern softwood pulp wetlaid to about 0.17 g/cc density, and one 68 gsm layer of a 50:50 blend by weight of Buckeye HP2 pulp and Kimberly-Clark 1654 pulp at about 0.17 g/cc density. The three layers of distribution material were plied together while the 68 gsm layer was adhesively attached to the retention zones and multifunctional material.

In the Examples the retention material in the intermediate retention zones and the retention material in the end retention zones represent absorbent composites with progressively greater capillarity further from the target zone. This provides progressively greater desorption of the distribution material, so that the intermediate retention zone material and the end retention zone material will fill according to specified design criteria for the absorbent system.

Filling approach can be adjusted by the distribution material flux and liquid transfer level as well as by the uptake rate of the absorbent composites in the intermediate and end retention zones. Compositionally these zones contain 60 weight percent particulate superabsorbent, such as Stockhausen FAVOR 870, and 40 weight percent cellulose pulp of a standard soft-wood fluffing grade such as Kimberly-Clark Corporation's Coosa Mills CR-1654. The retention material in the intermediate retention zones was cold compressed to a density of 0.2 g/cc. The retention material in the end retention zones was treated with 20 weight percent of a 1% KYMENE 557LX Binder aqueous solution and then hot pressed to a density of 0.2 g/cc. The retention material in the intermediate and end zones were adhesively attached to the top layer of distribution material 11 in the positions shown in FIG. 3. Composition of the five retention zones in this Example 1 is shown in Table 2.

Absorbent components stabilized with KYMENE 557LX binder were prepared as follows: A predetermined amount of superabsorbent and fluff fiber were blended and airformed into a sheet structure using a laboratory hand sheet former at, for example, a basis weight of between about 100 and 250 gsm. Sufficient layers of the sheet structures were prepared to achieve the desired component basis weight by plying. Each layer was sprayed with about 10 weight percent of an aqueous solution containing 0.24 weight percent KYMENE 557LX binder. The plys were layered after spraying and immediately compressed to the desired density while curing at 110° C. Heating may be carried out in, for example, a heated carver press.

EXAMPLE 2

Example 2 represents an embodiment of the invention that effectively moves liquid away from the target zone during each liquid insult, but preferentially fills from the bottom as current commercial products fill. Example 2 used the same surge and distribution material used in Example 1. The retention material composition is similar in all five zones for this Example 2, consisting of 60 weight percent Stockhausen FAVOR 870 particulate superabsorbent with 40 weight percent pulp fiber which was Kimberly-Clark Corporation's Coosa CR 1654. Table 2 shows the retention materials for Example 2.

EXAMPLE 3

Example 3 demonstrates a novel aspect of liquid placement control where a substantially liquid free zone is created within the absorbent product. The presence of a substantially liquid free zone can be used for some other additional functional purpose such as to create a region of enhanced dryness, higher air circulation or a void area for storage of BM. The location of the substantially liquid free zone can be anywhere in the absorbent product.

In Example 3, the substantially liquid free zone is located in the back intermediate zone position. The back intermediate zone was selected to demonstrate the ability of the current invention to control liquid placement on both sides of the substantially liquid free zone. Example 3 was also designed to give a uniform fill progression and final fill pattern in the four remaining zones. In this example, the distribution material was continuous through the substantially liquid free back intermediate zone which resulted in limited liquid being present within back intermediate zone. Alternatively, the distribution material can be positioned to one or more sides of the substantially liquid free zone, or the distribution material can be fully isolated from the substantially liquid free zone by a localized barrier such as a film, breathable film or melt blown barrier fabric.

The surge material, distribution material, and multifunctional material described in Example 1 are the same for Example 3. The composition of the retention material in the retention zones for Example 3 is the same as described in Example 1. Table 2 shows specific compositions for the retention materials.

EXAMPLE 4

Example 4 demonstrates an expanded substantially liquid free region in an absorbent product where the entire front or back portion of the product does not store liquid and can be used for some other purpose or designed attribute. Example 4 shows one execution of this aspect of the current invention where liquid is stored only in the center target zone and in the front intermediate and front end zones. This front fill pattern also shows a uniform fill progression in Example 4 as a demonstration of the liquid filling control provided by the current invention. The substantially liquid free region could be located anywhere in the absorbent product including the front or crotch regions. Alternative fill patterns, and progression can also be designed.

Example 4 uses the surge and distribution material and multifunctional material described in Example 1 and shown in FIG. 3. The position of the surge and distribution materials are the same as shown in FIG. 3, but can be shifted to completely isolate the substantially liquid free region from insult liquid or distributed liquid by totally removing either component from this region.

Example 4, as tested, contains liquid within the distribution material adjacent to back intermediate and back end zones showing that liquid storage would be possible with the appropriately designed retention materials and system design. The retention materials for Example 4 are compositionally the same as described for Example 1. Details for the Example 4 retention materials are shown in Table 2. The center zone and front intermediate and front end retention zones materials are attached to the distribution material as described for Example 1. The back intermediate and back end zone retention positions are left void, hence in Table 1 there is no entry for a fill ratio for the center back end zone (e.g. 3:5) ratio. The center:front end zone (e.g. 3:1) fill ratio of Example 4 as shown in Table 1 does fall within the inventive range. The surge material was place symmetrically over the center zone as shown in FIG. 3, partially overlapping the front intermediate zone retention material and the back intermediate zone void area.

EXAMPLE 5

This example illustrates one extreme to which a structure can achieve remote location of liquid via effective selection and assembly of materials providing surge, distribution and retention functions as described by this invention.

As mentioned above, the movement of liquid into and throughout the absorbent system is controlled by a capillarity difference from one material relative to another throughout the life cycle of the system. As also mentioned above, the amounts of contact area between distribution and retention materials greatly affects liquid transfer rates between them. In Example 5, increased distribution materials-retention material contact area is provided by alternating layers of these materials in zones of the product where both materials are located.

Structures provided by this invention can be arranged to provide a substantially liquid free zone which can be used for some other additional purpose or designed attribute such as to create a region of enhanced dryness, higher air circulation or a void area for storage of feces. The location of the substantially liquid free zone can be anywhere in the absorbent product depending on its functional purpose. In Example 5 this substantially liquid free zone is located in the back of the product in the back intermediate zone and back end zone to provide enhanced dryness and skin health in the crotch area, also resulting in a zone 3:1 fill ratio less than 1.0.

Example 5 was assembled to achieve a fill pattern of liquid stored entirely in the front portion of a shaped absorbent product with a crotch width of 6.35 cm (2.5 inches). The longitudinal dimension of the absorbent was 31.75 cm (12.5 inches) and the transverse dimension varied in each zone. The product was divided transversely into five zones to determine the fill ratio, each zone equal to one fifth of the overall absorbent length. As a result of the varying transverse dimension in such a shaped product, each zone contains different areas of absorbent materials as measured in square centimeters. For Example 5 the area of absorbent structure per zone was as follows: end zone 1—76 cm$^2$, intermediate zone 2—57.3 cm$^2$, center target zone 3—45.25 cm$^2$, intermediate zone 4—78.65 cm$^2$, and end zone 5—77.4 cm$^2$.

The surge material used in Example 5 was composed of a pulp coform material. The web comprised a blend of 50 percent cellulosic fluff available as IP Supersoft from International Paper Corporation and 50 percent macrofiber meltblown fibers of polypropylene, using resin available in pellet form from Himont U.S.A. Inc. of Wilmington Del. (now operating as Montell). The web was spray treated during formation with a solution of TRITON X102 surfactant to obtain an addition rate of 0.5 weight percent. The meltblown polypropylene was believed to have fiber sizes ranging from about 10–113 microns and an average fiber size of 50.2 microns. The web had a basis weight of 194 gsm, a density of 0.037 g/cm$^3$ and was formed in accordance with the process described in U.S. Pat. No. 4,100,324 to Anderson and Sokolowski.

The surge material was placed subjacent the liner material which was composed of 100% polypropylene spunbond where the fibers had a bilobal cross-section and which is available from Kimberly-Clark Corporation. The liner material was prepared at 27 gsm using polypropylene resin from available in pellet form from Himont U.S.A. Inc. of Wilmington Del. (now operating as Montell). The liner material was made wettable using a liquid application system of three roll/reverse roll coating a solution of TRITON X-102 surfactant onto the spunbond liner to achieve an addition level of 0.25 weight percent.

The distribution material was compositionally the same as the surge material. In addition, the distribution material had been embossed using nipped, heated calendar rolls operating at 3 meters per minute with surface temperatures of top roll (which had a sine wave embossing surface) of 102° C. and bottom roll (which had a smooth surface) of 107° C. The fabric was passed through the nip, collected on a roll, then unwound and fed through the embossing nip a second time. The resultant embossed coform distribution material had a basis weight of 95 gsm and a web density of 0.075 g/cm$^3$. This material achieved an equilibrium vertical wicking height of 10.2 cm after 15 minutes.

The retention material was composed of 50 weight percent microfiber meltblown and 50 weight percent SANWET IM 1500 superabsorbent granules supplied by Hoechst Celanese Corporation of Charlotte, N.C. The meltblown was produced with polypropylene resin available in pellet form from Himont U.S.A. Inc. of Wilmington Del. (now operating as Montell). The web was spray treated during formation with a solution of TRITON X102 surfactant to obtain an addition rate of 0.5 weight percent. The superabsorbent meltblown retention material was prepared at 123 gsm, 0.106 g/cm$^3$ and had a saturated capacity in 8.5 g/l saline solution of 32 grams of liquid per gram of fabric tested.

To evaluate the absorbent system with human subjects, individual products were prepared. The shaped pieces of each component in this Example 5 were cut out, weighed and assembled. The product was assembled using multiple layers of each material type. Four layers of distribution material were prepared using the entire product shape, thus covering all five absorbent zones. Seven layers of retention material were cut to cover end zone 1 and intermediate zone 2. The distribution and retention materials were layered from the bottom (side away from a wearer) of the product as follows: 1 layer distribution, 3 layers retention, 1 layer distribution, 2 layers retention, 1 layer distribution, 2 layers retention, 1 layer distribution. To prevent shifting of the shorter retention material, the layers were bonded together using localized ultrasonic bond points. In addition, sonic bonding lines parallel to the longitudinal axis of the product were added to sustain the connection between the layers. Approximately 580 cm$^2$ of contact area were achieved between layers of distribution and layers of retention materials.

One moderate sized distribution layer covering end zone 1, intermediate zone 2, center target zone 3 and intermediate zone 4 was placed on top of the distribution/retention laminate. A smaller distribution material was placed on top which had been cut to cover intermediate zone 2, center target zone 3 and intermediate zone 4. Finally three layers of surge material were cut to cover end zone 1, intermediate zone 2, center target zone 3 and intermediate zone 4. The completed assembly was covered by the spunbond liner which was thermally sealed around the edges to a polyeythylene polymer film.

Three diapers with this absorbent system were tested on infants who weighed about 12–15 pounds. Body temperature (37° C. or 98.6° F.) saline (a solution of 8.5 grams of sodium chloride per liter) was supplied to the target area of each diaper with an insult of 60 ml at a flow rate of 15 cc/sec through a piece of plastic tubing with about 0.3175 cm (0.125 inch) inner diameter. One end of the tube was connected to a pumping apparatus and the other end was placed into the baby's diaper and positioned at the target zone. Aliquots of saline were added every 15 minutes until leakage occurred. The diapers were removed from the wearers and the absorbent systems were cut and weighed to determine the fill ratio. The three products contained 257, 242 grams and 259 grams of saline when leakage occurred, respectively.

The absorbent system was cut into 1 inch (2.54 cm) sections along the longitudinal axis of the product, beginning in the front of the product. When a 1 inch section was located across two zones, such as the end zone 1 and intermediate zone 2, it was assumed that fluid was equally located in both zones. Thus half of the fluid in that section was added to each zone total.

The average fluid per zone was as follows: end zone 1; 128.3 grams, intermediate zone 2; 23.25 grams, center target zone 3; 21.5 grams, intermediate zone 4; 9.5 grams, and end zone 5; 0 grams. This results in a zone 3:1 fill ratio of 0.16, or even less than 1:1, clearly demonstrating the invention's ability to achieve remote location of liquid via effective selection and assembly of materials which provide surge, distribution and retention functionalities.

Test results for Examples 1–4 is shown in Table 1. Table 1 describes the amount of liquid in grams in each zone after each insult where N is the number of trials, the run-off amount in milliliters after each insult and in total, a calculated weight ratio of liquid in the center zone to each end zone and a saturated capacity in grams. Note that in the Tables, the center front end ratio is labeled 3:1 and the center:back end ratio is labeled 3:5 and the zones are numbered 1–5 from front to back with the center zone being zone number 3. The amount of liquid in grams in each zone after insult was determined by x-ray imaging as discussed in the Test Methods section.

Table 2 shows the materials of construction for liquid retention in each of the zones in Example 1–4. Note that Examples 3 and 4 which had void storage areas show no composition in Table 2. In Table 2 the basis weight in grams per square meter (gsm) of the material used in the Example is given first, the superabsorbent by weight percent is next, followed by the pulp weight percent, the stabilization method and the density in grams/cubic centimeter. FAVOR 870 is superabsorbent commercially available from the Stockhausen Company of Greensboro, N.C. 27406 and is a highly crosslinked surface superabsorbent. AFA 94-21-5 is a 850 to 1400 micron suspension polymerized polyacrylate particle from The Dow Chemical Company of Midland, Mich. CR 1654 pulp is commercially available from the Kimberly-Clark Corporation of Dallas, Tex. and is a southern softwood pulp. HBAFF is available from the Weyerhaeuser Corporation of Tacoma, Wash., and is a high bulk additive formaldehyde free pulp which is a crosslinked southern softwood pulp fiber with enhanced wet modulus. HBAFF has a chemical treatment which sets in a curl and twist, in addition to imparting added dry and wet stiffness and resilience to the fiber. The "3% Binder" referred to in Table 2 is a binder fiber used to mechanically stabilize the absorbent structure and is from Danaklon a/s, located at Engdraget 22, KD-6800 Varde, Denmark, and is 2 denier conjugate PE/PP sheath/core fibers cut into 6 mm lengths. KYMENE 557LX binder is a liquid binder available from Hercules Inc. of Wilmington, Del.

TABLE I

|  |  | Liquid Retained (g) | | | | | Run-off (ml) | | | | Zone Ratio | | Saturated |
| --- | --- | --- | --- | --- | --- | --- | --- | --- | --- | --- | --- | --- | --- |
|  | N= | Zone 1 | Zone 2 | Zone 3 | Zone 4 | Zone 5 | $1^{st}$ | $2^{nd}$ | $3^{rd}$ | Total | 3:1 | 3:5 | Capacity (g) |
| Example 1 | 6 | | | | | | | | | | | | 405 |
| $1^{st}$ Insult | | 9.31 | 18.13 | 19.70 | 18.67 | 9.69 | 4.52 | | | 4.52 | 2.1 | 2.0 | |
| $2^{nd}$ Insult | | 20.88 | 30.23 | 36.98 | 33.67 | 22.79 | | 10.95 | | 15.47 | 1.8 | 1.6 | |
| $3^{rd}$ Insult | | 31.38 | 45.96 | 55.49 | 41.61 | 28.49 | | | 21.62 | 37.09 | 1.8 | 1.9 | |
| Example 2 | 3 | | | | | | | | | | | | 376 |
| $1^{st}$ Insult | | 6.22 | 17.96 | 30.36 | 15.03 | 6.57 | 3.87 | | | 3.87 | 4.9 | 4.6 | |
| $2^{nd}$ Insult | | 13.06 | 36.02 | 50.17 | 33.20 | 13.25 | | 10.43 | | 14.30 | 3.8 | 3.8 | |
| $3^{rd}$ Insult | | 20.01 | 49.94 | 69.15 | 44.73 | 22.40 | | | 17.47 | 31.77 | 3.1 | 3.1 | |
| Example 3 | 3 | | | | | | | | | | | | 427 |
| $1^{st}$ Insult | | 14.01 | 18.85 | 22.12 | 6.00* | 15.35 | 3.67 | | | 3.67 | 1.6 | 1.4 | |
| $2^{nd}$ Insult | | 32.46 | 37.78 | 41.44 | 9.47* | 28.62 | | 6.56 | | 10.23 | 1.3 | 1.4 | |
| $3^{rd}$ Insult | | 44.82 | 51.55 | 62.74 | 13.92* | 38.38 | | | 18.37 | 28.60 | 1.4 | 1.6 | |
| Example 4 | 3 | | | | | | | | | | | | 389 |
| $1^{st}$ Insult | | 16.09 | 21.45 | 30.66 | 6.91* | 3.79* | 1.10 | | | 1.60 | 1.9 | — | |
| $2^{nd}$ Insult | | 32.91 | 45.09 | 55.80 | 13.00* | 6.80* | | 5.30 | | 6.40 | 1.7 | — | |
| $3^{rd}$ Insult | | 52.70 | 65.37 | 73.07 | 14.68* | 7.95* | | | 19.83 | 26.23 | 1.4 | — | |

*= Designates absence of retention in the zone

TABLE 2

STORAGE COMPOSITE COMPOSITION

|  | Zone 1 RETENTION | Zone 2 RETENTION | Zone 3 MULTIFUNC. | Zone 4 RETENTION | Zone 5 RETENTION |
| --- | --- | --- | --- | --- | --- |
| Example 1 | 635 gsm | 497 gsm | 389 gsm | 497 gsm | 635 gsm |
|  | 60% FAVOR 870 superabsorbant | 60% Favor 870 | 40% AFA 94-21-5 | 60% Favor 870 | 60% Favor 870 |
|  | 40% CR 1654 | 37% CR 1654 | 57% HBADD | 37% CR 1654 | 40% CR 1654 |
|  | Kymene Stabilized | 3% Binder | 3% Binder | 3% Binder | Kymene Stabilized |
|  | 0.2 g/cc | 0.2 g/cc | 0.1 g/cc | 0.02 g/cc | 0.2 g/cc |
| Example 2 | 552 gsm | 497 gsm | 476 gsm | 497 gsm | 552 gsm |
|  | 60% Favor 870 | 60% Favor 870 | 60% Favor 870 | 60% Favor 870 | 60% Favor 870 |
|  | 37% CR 1654 | 37% CR 1654 | 37% CR 1654 | 37% CR 1654 | 37% CR 1654 |
|  | 3% Binder | 3% Binder | 3% Binder | 3% Binder | 3% Binder |
|  | 0.2 g/cc | 0.2 g/cc | 0.1 g/cc | 0.2 g/cc | 0.2 g/cc |
| Example 3 | 794 gsm | 621 gsm | 486 gsm | NONE | 794 gsm |
|  | 60% Favor 870 | 60% Favor 870 | 40% AFA 94-21-5 | | 60% Favor 870 |
|  | 40% CR 1654 | 37% CR 1654 | 57% HBAFF | | 40% CR 1654 |
|  | Kymeme Stabilized | 3% Binder | 3% Binder | | Kymene Stabilized |
|  | 0.2 g/cc | 0.2 g/cc | 0.1 g/cc | | 0.2 g/cc |
| Example 4 | 1104 gsm | 863 gsm | 676 gsm | NONE | NONE |
|  | 60% Favor 870 | 60% Favor 870 | 40% AFA 94-21-5 | | |
|  | 40% CR 1654 | 37% CR 1654 | 57% HBAFF | | |
|  | Kymene Stabilized | 3% Binder | 3% Binder | | |
|  | 0.2 g/cc | 0.2 g/cc | 0.1 g/cc | | |

The above results show that absorbent articles with low fill ratio can be successfully produced according to this invention. In order to illustrate the magnitude of the improvement this invention brings to the field of personal care products and liquid transport and storage, comparative data was gathered on a number of commercially available diapers. The diapers were tested after each of three insults of 80 ml each separated by 30 minutes according to the MIST Evaluation Test. Each type of diaper was tested three times. The diaper saturated capacity (S.C.) in grams was also determined. Table 3 shows the liquid distribution in each zone as determined by X-ray imaging and also includes the runoff and actual load. The data in Table 3 is in milliliters. Table 4 shows the fill ratios using the data of Table 3. Table 5 shows the liquid partitioning and zone ratios for the same types of diapers using the cut and weigh method. Table 6 shows the liquid partitioning and zone ratios after each of three insults for Example 1 and two commercial diapers using the cut and weigh method. The data quite strikingly shows the difference in fill ratios between the invention and current commercial diapers for the typical commercially available wide crotch diaper. The diapers tested were all on the market in summer of 1995. Note that the amount of liquid in each zone used to develop the data in Table 3A was determined according to X-ray imaging. The data in Table 3B was determined by the cut and weigh method.

HUGGIES and KLEENEX are trademarks of the Kimberly-Clark Corporation of Dallas, Tex., which may be contacted at Dept. HC3G-32, PO Box 2020, Neenah, Wis. 54957-2020. The KLEENEX HUGGIES diapers tested were ULTRATRIM diapers for Her, step 3, medium (16–28 pounds) and ULTRATRIM diapers for Him, step 3, medium (16–28 pounds).

PAMPERS and LUVS are trademarks of the Procter and Gamble Corporation of Cincinnati, Ohio. The PAMPERS diapers tested were PAMPERS Stretch Boy, size 3 (16–28 pounds). The LUVS diapers tested were ultra leakguards size 3 (16–28 pounds) for boys and girls.

WONDER DRYS is a trademark of Paragon Trade Brands, 33325 8$^{th}$ Avenue South, Federal Way, Wash. 98003. The WONDER DRYS diapers tested were ultrathins medium (12–24 pounds), boys and girls.

DRYPERS is a trademark of Drypers Corporation, PO Box 8830, Vancouver, Wash. 98666-8830. The DRYPERS diapers tested were size medium, (12–24 pounds) boys and girls.

LOVING TOUCH is a trademark of Paragon Trade Brands. The LOVING TOUCH diapers tested were basic style medium (12–24 pounds), boys and girls and ultrathin medium size 3 (12–24 pounds) for boys and girls.

FITTI is a trademark of Associated Hygienic Products, LLC, Duluth Ga., 30136. The FITTI diapers tested were medium (12–24 pounds) boys and girls.

TABLE 3

|  | Zone 1 | Zone 2 | Zone 3 | Zone 4 | Zone 5 | Actual Load | Runoff |
|---|---|---|---|---|---|---|---|
| HUGGIES HER |  |  |  |  |  |  |  |
| 1$^{st}$ Insult | 1.58 | 10.70 | 43.50 | 12.36 | 0.30 | 68.45 | 11.55 |
| 2$^{nd}$ Insult | 1.60 | 31.01 | 65.66 | 29.45 | 0.45 | 128.17 | 31.83 |
| 3$^{rd}$ Insult | 2.14 | 52.59 | 73.77 | 47.70 | 1.01 | 177.2 | 62.80 |
| HUGGIES HIM |  |  |  |  |  |  |  |
| 1$^{st}$ Insult | 0.96 | 11.07 | 49.84 | 12.51 | 0.25 | 74.63 | 5.12 |

TABLE 3-continued

|  | Zone 1 | Zone 2 | Zone 3 | Zone 4 | Zone 5 | Actual Load | Runoff |
|---|---|---|---|---|---|---|---|
| 2$^{nd}$ Insult | 1.67 | 37.22 | 65.73 | 31.24 | 0.41 | 136.26 | 23.74 |
| 3$^{rd}$ Insult | 2.66 | 60.37 | 72.69 | 46.73 | 2.08 | 184.53 | 55.47 |
| WONDER DRYS ULTRA |  |  |  |  |  |  |  |
| 1$^{st}$ Insult | 3.94 | 18.75 | 31.51 | 15.29 | 2.88 | 72.37 | 7.63 |
| 2$^{nd}$ Insult | 7.44 | 35.10 | 44.27 | 35.99 | 3.97 | 126.77 | 33.23 |
| 3$^{rd}$ Insult | 17.18 | 49.22 | 49.73 | 51.51 | 6.46 | 174.10 | 65.90 |
| PAMPERS STRETCH BOYS |  |  |  |  |  |  |  |
| 1$^{st}$ Insult | 2.07 | 14.97 | 48.56 | 11.57 | 1.99 | 79.17 | 0.83 |
| 2$^{nd}$ Insult | 2.33 | 31.67 | 75.17 | 30.66 | 2.10 | 141.90 | 18.10 |
| 3$^{rd}$ Insult | 4.34 | 53.41 | 85.66 | 46.73 | 2.88 | 193.03 | 46.97 |
| LUVS ULTRA |  |  |  |  |  |  |  |
| 1$^{st}$ Insult | 5.30 | 15.66 | 39.19 | 14.93 | 4.03 | 79.10 | 0.90 |
| 2$^{nd}$ Insult | 6.12 | 32.94 | 62.90 | 35.48 | 4.96 | 142.40 | 17.60 |
| 3$^{rd}$ Insult | 8.68 | 52.07 | 71.85 | 51.00 | 6.26 | 189.87 | 50.13 |
| DRYPERS |  |  |  |  |  |  |  |
| 1$^{st}$ Insult | 2.33 | 14.93 | 45.40 | 14.46 | 1.62 | 78.73 | 1.27 |
| 2$^{nd}$ Insult | 2.30 | 30.53 | 71.04 | 25.69 | 1.67 | 131.23 | 28.77 |
| 3$^{rd}$ Insult | 3.64 | 45.58 | 82.69 | 36.11 | 1.81 | 169.83 | 70.17 |
| LOVING TOUCH BASIC |  |  |  |  |  |  |  |
| 1$^{st}$ Insult | 1.38 | 18.30 | 46.78 | 12.25 | 0.43 | 79.13 | .087 |
| 2$^{nd}$ Insult | 3.28 | 44.46 | 60.09 | 31.55 | 0.46 | 139.83 | 20.17 |
| 3$^{rd}$ Insult | 15.49 | 60.74 | 67.40 | 45.39 | 0.68 | 189.70 | 50.30 |
| LOVING TOUCH ULTRA THIN |  |  |  |  |  |  |  |
| 1$^{st}$ Insult | 1.61 | 21.53 | 38.69 | 7.00 | 1.20 | 70.03 | 9.97 |
| 2$^{nd}$ Insult | 3.02 | 47.40 | 55.92 | 15.17 | 1.16 | 122.67 | 37.33 |
| 3$^{rd}$ Insult | 6.03 | 63.58 | 63.32 | 27.50 | 1.18 | 161.60 | 78.40 |
| FITTI BOY & GIRL |  |  |  |  |  |  |  |
| 1$^{st}$ Insult | 1.17 | 12.24 | 54.54 | 10.52 | 0.87 | 79.33 | 0.67 |
| 2$^{nd}$ Insult | 1.03 | 36.17 | 83.24 | 22.74 | 0.72 | 143.90 | 16.10 |
| 3$^{rd}$ Insult | .092 | 59.66 | 96.79 | 41.64 | 0.69 | 199.70 | 40.30 |

TABLE 4

|  | 1st Insult | | 2nd Insult | | 3rd Insult | | |
|---|---|---|---|---|---|---|---|
|  | Zone 3:1 | Zone 3:5 | Zone 3:1 | Zone 3:5 | Zone 3:1 | Zone 3:5 | S.C. Gm |
| HUGGIES HER | 28 | 145 | 41 | 146 | 35 | 73 | 386 |
| HUGGIES HIM | 52 | 200 | 39 | 160 | 27 | 35 | 391 |
| WONDER DRYS ULTRA | 8 | 11 | 6 | 11 | 3 | 8 | 374 |
| PAMPERS STRETCH BOYS | 24 | 24 | 32 | 36 | 20 | 30 | 480 |
| LUVS ULTRA | 8 | 10 | 10 | 13 | 8 | 12 | 494 |
| DRYPERS | 20 | 28 | 31 | 43 | 23 | 46 | 460 |
| LOVING TOUCH BASIC | 34 | 109 | 18 | 131 | 4 | 99 | 415 |
| LOVING TOUCH ULTRATHIN | 24 | 32 | 19 | 48 | 11 | 54 | 393 |
| FITTI BOY & GIRL | 47 | 63 | 81 | 116 | 105 | 140 | 563 |

TABLE 5

Liquid retained in grams after the 3rd Insult

|  | Zone 1 | Zone 2 | Zone 3 | Zone 4 | Zone 5 | 3rd insult fill ratio 3:1 | 3rd insult fill ratio 3:5 |
|---|---|---|---|---|---|---|---|
| HUGGIES HER | 1.2 | 53.8 | 65.3 | 45.4 | 1.4 | 54.4 | 46.6 |
| HUGGIES HIM | 2.7 | 60.3 | 72.6 | 46.7 | 2.1 | 26.9 | 34.6 |
| WONDER DRYS ULTRA | 20.1 | 50.6 | 52.1 | 49.6 | 3.4 | 2.6 | 15.3 |
| PAMPERS STRETCH BOYS | 2.5 | 54.3 | 83.6 | 46.8 | 1 | 33.4 | 83.6 |
| LUVS ULTRA | 6 | 54.3 | 71.6 | 48.1 | 2.1 | 11.9 | 34 |
| DRYPERS | 2.2 | 44.5 | 75.7 | 39.2 | 0.4 | 34.4 | 189.3 |
| LOVING TOUCH BASIC | 13.7 | 58.3 | 61.9 | 44.9 | 1.2 | 4.5 | 51.6 |
| LOVING TOUCH ULTRATHIN | 7.9 | 62.7 | 59.6 | 23.2 | 0.2 | 7.5 | 298 |
| FITTI BOY & GIRL | 0.5 | 49.2 | 91.4 | 49.4 | 0.2 | 182 | 457 |

TABLE 6

Liquid retained in grams after each Insult

|  | Zone 1 | Zone 2 | Zone 3 | Zone 4 | Zone 5 | Fill ratio 3:1 | Fill ratio 3:5 |
|---|---|---|---|---|---|---|---|
| Example 1 | | | | | | | |
| 1st Insult | 6.4 | 23.2 | 19.3 | 18.1 | 7.9 | 3.0 | 2.4 |
| 2nd Insult | 21.8 | 28.9 | 43.4 | 30.4 | 22.4 | 2.0 | 1.9 |
| 3rd Insult | 32.6 | 46.7 | 59.9 | 38.8 | 30.5 | 1.8 | 2.0 |
| HUGGIES HER | | | | | | | |
| 1st Insult | 0.4 | 11.3 | 46.0 | 9.31 | 0.3 | 115 | 153 |
| 2nd Insult | 0.7 | 42.1 | 60.4 | 27.5 | 0.3 | 86.3 | 20.1 |
| 3rd Insult | 1.2 | 53.8 | 65.3 | 45.4 | 1.4 | 54.4 | 46.6 |
| WONDER DRYS ULTRA | | | | | | | |
| 1st Insult | 0.3 | 16.1 | 42.9 | 18.9 | 0.3 | 143 | 143 |
| 2nd Insult | 2.5 | 39.9 | 54.6 | 36.9 | 0.9 | 21.8 | 60.7 |
| 3rd Insult | 20.1 | 50.6 | 52.1 | 49.6 | 3.4 | 2.6 | 15.3 |

As can be seen from the above results, there is herein provided an absorbent article wherein much of an insult is moved away from the target zone. This provides a great advance in absorbent technology and personal care product design. In addition, runoff is greatly reduced in comparison with conventional personal care products.

As will be appreciated by those skilled in the art, changes and variations to the invention are considered to be within the ability of those skilled in the art. Such changes and variations are intended by the Inventors to be within the scope of the invention.

What is claimed is:

1. A personal care product comprising an absorbent system having functions of intake, controlled release, distribution, transfer and final storage and comprising a surge layer, a distribution layer and a retention layer which are in sufficient contact to transfer liquid between them, wherein said surge layer is capable of handling an incoming liquid insult of between about 60 and 100 cc at a volumetric rate of from about 5 to 20 cc/sec and has a capillary tension, said distribution layer has a capillary tension higher than the capillary tension of said surge layer and an equilibrium wicking height capillary tension of at least about 15 cm as measured by the wicking of a 8.5 g/l saline solution according to the Vertical Liquid Flux rate test throughout a life cycle of the absorbent system, said retention layer absorbs liquid quickly and efficiently from said distribution layer in a controlled manner such that liquid may be stored in a desired pattern and has a capillary tension higher than the capillary tension of the distribution layer throughout the life cycle of the absorbent system and is mechanically stabilized, said absorbent system divided transversely into a center zone adjacent two intermediate zones which are each adjacent an end zone wherein said zones are about equally sized, and said absorbent system having a ratio of an amount of liquid stored in the center zone to an amount of liquid stored in at least one of said end zones 30 minutes after each of three insults of 80 ml according to a MIST Evaluation Test which defines a fill ratio of less than 5:1, and a fully saturated capacity of less than 450 g.

2. The personal care product of claim 1 wherein said first insult.

3. The personal care product of claim 1 wherein every one of said three insults of 80 ml are separated by 30 minutes.

4. The personal care product of claim 1 having less than 40 ml of total run-off from said three 80 ml insults.

* * * * *

UNITED STATES PATENT AND TRADEMARK OFFICE
CERTIFICATE OF CORRECTION

PATENT NO. : 6,152,904  
DATED : November 28, 2000  
INVENTOR(S) : Billie J. Matthews et al.

Page 1 of 1

It is certified that error appears in the above-identified patent and that said Letters Patent is hereby corrected as shown below:

<u>Column 2,</u>  
Line 10, "filly" should read -- fully --  
Line 60, "worm" should read -- worn --

<u>Column 28, claim 2,</u>  
Lines 40-41, should read -- The personal care product of claim 1 wherein said second insult of 80 ml is delivered 30 minutes after said first insult. --

Signed and Sealed this

Second Day of April, 2002

*Attest:*

JAMES E. ROGAN  
*Attesting Officer*     *Director of the United States Patent and Trademark Office*